United States Patent
Serikov (10) Patent No.: US 6,602,391 B2
(45) Date of Patent: Aug. 5, 2003

(54) APPARATUS AND METHOD FOR COMBINED CAPILLARY SEPARATION AND BLOTTING OF BIOLOGICAL MACROMOLECULES

(76) Inventor: Vladimir B. Serikov, Dept. Physiology, UC Davis, One Shields Ave., Davis, CA (US) 95616

( * ) Notice: Subject to any disclaimer, the term of this patent is extended or adjusted under 35 U.S.C. 154(b) by 278 days.

(21) Appl. No.: 09/734,452

(22) Filed: Mar. 5, 2001

(65) Prior Publication Data

US 2002/0166769 A1 Nov. 14, 2002

(51) Int. Cl.[7] .................. G01N 27/447; G01N 27/453
(52) U.S. Cl. ................. 204/464; 204/455; 204/605; 204/613; 204/451; 204/601
(58) Field of Search ................... 204/455, 456, 204/462, 464, 605, 613, 614, 451, 601; 422/70

(56) References Cited

U.S. PATENT DOCUMENTS

| | | |
|---|---|---|
| 4,589,965 A | 5/1986 | Kreisher |
| 4,994,166 A | 2/1991 | Fernwood et al. |
| 5,013,420 A | 5/1991 | Schuette |
| 5,039,493 A | 8/1991 | Oprandy |
| 5,149,408 A | 9/1992 | Perlman |
| 5,155,049 A | 10/1992 | Kauvar et al. |
| 5,160,626 A | 11/1992 | Pemawansa et al. |
| 5,279,721 A | 1/1994 | Schmid |
| 5,284,559 A | 2/1994 | Lim et al. |
| 5,449,446 A * | 9/1995 | Verma et al. ............. 204/612 |
| 5,593,561 A | 1/1997 | Cognard et al. |
| 5,840,169 A | 11/1998 | Andersen |
| 5,897,817 A | 4/1999 | Radovich et al. |
| 5,985,121 A | 11/1999 | Wu et al. |

* cited by examiner

Primary Examiner—Nam Nguyen
Assistant Examiner—Alex Noguerola (57) ABSTRACT

An apparatus and method are described for capillary separation of macromolecules and precise post-separation blotting. Apparatus include disposable separating element (capillary), which contains a sieving or interaction matrix inside, an external layer of blotting material, positioned close to the boundary of said sieving or interaction matrix, and the membrane with changeable permeability for separated material; said membrane separates blotting layer from the sieving or interaction matrix. After separation of macromolecules in capillary with initially non-permeable walls, chemical or physical modification of the membrane is performed, which is followed by changing the vector of driving forces for transfer, so that separated molecules are moved through the walls of the capillary and blotted to the outer layer of separating element, which contains blotting material. Means of modification of the membrane include chemical or physical modification, leading to changes in permeability. Change in driving forces may include electrical charge application, bulk flow of fluid or hydrostatic pressure.

4 Claims, 3 Drawing Sheets

APPARATUS AND METHOD FOR COMBINED CAPILLARY SEPARATION AND BLOTTING OF BIOLOGICAL MACROMOLECULES

BACKGROUND OF THE INVENTION

The present invention relates generally to devices and methods for performing separation of biological macromolecules (electrophoresis or gel chromatography) and transfer (electro-blot, capillary blot or other means of blotting). The present invention particularly relates to a device, which can perform separation and blotting of protein and nucleic acid samples within one capillary element.

Separation of macromolecules such as proteins and nucleic acids is a necessary step in numerous applications of protein and DNA-RNA analyses in multiple biological, scientific, medical, and forensic applications. The most prominent and widely used techniques for separating macromolecules are chromatography and gel electrophoresis. Following separation by said principles, proteins and nucleic acids are then generally collected in separate volumes or fixed (blotted) to special chemical compounds, mostly nitrocellulose or nylon (F. Ausubel et al (Ed.), *Current Protocols in Molecular Biology*, Ed. Current Protocols, Wiley, N.Y., 1994), for further processing and analyses. Separation and blotting must be performed independently in time and space, otherwise highly chemically reactive blotting membrane may be contaminated with separated molecules. For this reason after separation is performed, the gel with separated molecules is placed in contact with blotting membrane by mechanical transfer.

Electrophoresis, used for separation, utilizes a physical phenomenon of charged particles' ability to migrate toward the pole possessing the charge opposite to that of a particle, when it is suspended between opposite poles in an electric field. Conventional gel electrophoresis utilizes a gel slab assembly. Pore matrix of a gel slab is usually made of agarose or polyacrialamide. Pores, which retain macromolecules depending on their physical properties (size, hydrodynamic radius, weight, composition, electrical charge, etc.), form an interacting or sieving matrix. Wells are formed in the upper part of the gel slab during casting procedure. A gel slab assembly is placed into a device for electrophoresis. Samples are then introduced in a band within wells; and an electric field is applied across the slab. The upper and the lower portions of the gel are submerged into separate buffer solution reservoirs. The electric field forces macromolecules of the samples to migrate through the gel. During migration, the macromolecules are "sieved" by their properties, most often their molecular weight. Specific species of macromolecules will be in bands arranged from top to bottom of the gel (Andrews, A. T. *Electrophoresis: Theory, Techniques, and Biochemical and Clinical Applications*. Clarendon Press-Oxford (1986), $2^{nd}$ Ed).

In the process of DNA separation, the DNA fragments (DNA ladders) can be labeled before or after separation with either radioactive or florescence labels (F. Ausubel et al (Ed.), *Current Protocols in Molecular Biology*. Current Protocols, Wiley, N.Y., 1994, Chapter 2). In DNA sequencing procedures, each of the four types of a nucleotide can be labeled with specific probe, which will appear at termination of DNA fragment. A mixture of different reactions can be electrophorized and separated according to the label from one reservoir in the gel.

After separation is complete, deposition membrane with blotting material is placed in contact with gel. A common transfer process is called "electro-blot" transfer. In the "electro-blot" transfer process, the macromolecules in the gel slab move under an electric field to a blotting membrane. In designing an electro-blot transfer system it is essential that the blotting membrane be in close contact with the gel slab. Presence of gas bubbles between the gel slab and blotting membrane will prevent the band images from being transferred properly. It is also important to maintain a uniform electric field across the electro-blot sandwich. Transfer of the gel slab onto the nitrocellulose membrane must be carefully performed so that the macromolecules on the gel membrane are not removed or contaminated. After transfer, a labeling procedure must be employed, and a detection technique must be utilized so that the samples can be analyzed. A commonly used detection method involves staining and de-staining of the gel slab. This technique imposes staining of the entire gel with a dye that only adheres to the macromolecules. Then a de-staining process is performed, wherein dye not adhered to the macromolecules is washed away; bands of macromolecules thus become detectable. Another common detection method is the use of antibodies. Bands of proteins or samples are blotted or transferred to a binding membrane, which binds macromolecules. Then, a known antibody is introduced. The antibody combines with a specific protein if it is present in a sample. In order to detect the antibody-protein combination, the antibodies are labeled with fluorescent or radioactive tags or have enzyme activity, which is further detected by separate methods (F. Ausubel et al (Ed.), *Current Protocols in Molecular Biology*, Ed. Current Protocols, Wiley, N.Y., 1994, Chapter 10).

Capillary electrophoresis offers some advantages not available with other separation methods, such as slab gel separation, HPLC, or column chromatography (Krylov, S. N., and Dovichi, N. J. Capillary electrophoresis for the analyses of biopolymers. *Analytical Chemistry*, 2000, Vol. 72, No. 12:111R-128R). The major advantage of the capillary electrophoresis is the speed of the analysis (few minutes, compared to few hours by other methods). Highly efficient dissipation of electro-resistive generated heat in the capillary is provided by a large surface to volume ratio. Decoupling of gel temperature from electro-resistive generated energy provides greater effective field strength. Migration rate varies directly with the field strength over a linear range, which can be extended using gel-filled capillaries. Thus, separations at higher fields can be performed with reduced running time. The advantage of a single capillary can be further extended by use of an array of coupled capillaries with equal characteristics. A possibility to process them together under identical conditions allows technology for protein separation and DNA sequencing (Dolnik V. DNA sequencing by capillary electrophoresis. *J Biochem. and Biophys. Methods.* 1999, V.41, No. 2–3:103–119).

Collection of samples in capillary electrophoresis poses, however, substantial technical problems (Altria, K. D. Overview of capillary electrophoresis and capillary chromatography. *J. Chromatography*, 1999, Vol. 286, No 1–2:443–63; Swinney, K., Bornhop, D. J. Detection in capillary electrophoresis. *Electrophoresis*, 2000, Vol. 21, no. 7:1239–50). Samples are eluted from the capillary at a certain point by either pressurized flow or electroelution. Method for sample collection by electroelution employs standard capillary electrophoretic equipment. Several parameters of the system must be precisely controlled (velocity of migration of a sample, distance between the detection point and the end of the capillary, etc). To collect fractions in appropriate vials, capillaries, etc, one must know the exact time, when a zone appears at the exit end of the capillary, as the variation of migration rates in capillary electrophoresis can be more than 2%. The time necessary for the zone of interest to move through the distance between the detection point and the capillary exit is calculated after detection of the zone of interest is done. Electric current is then turned off, and the capillary is removed from the apparatus and placed into a collection vial. Current is applied for a predetermined time so that the zone migrates into the collection reservoir with buffer from the capillary. Pressure can also be applied to remove the sample from the capillary. After collection of the zone is accomplished, the capillary is placed back into the electrophoretic device, and separation continues. A set of collection reservoirs, or capillaries, containing a collection buffer and electrode, can be positioned close to the exit end of the capillary; collection of samples can be performed, while the electric current is temporarily turned off.

Another approach for collecting samples from a capillary is positioning samples on a membrane. According to the technique, the exit end of the capillary is in contact with a wet surface of a moving blotting membrane, which also serves as an electrode. Separated proteins, or DNA fragments, are transferred to deposition membranes either by electrophoresing the bands onto a moving deposition membrane (direct electroblotting) or by various elution techniques implying gradient of hydrostatic pressure, capillary forces, and others. Standard direct blotting devices use a deposition membrane attached to a conveyor belt in the lower buffer chamber that remains totally submerged during electrophoresis. These devices require physical removal of the nylon or other membrane from the conveyor belt. Submersion of the deposition membrane makes detection and processing a difficult task.

Prior art:

U.S. Pat. No. 4,622,124 discloses a device for horizontal electroblotting of electrophoretically separated material. A liquid tight container is provided having a support assembly, horizontally disposed in a chamber defined by the container. Electrodes are located below and above the support assembly, and a barrier is provided to prevent bubble attachment and uneven blotting. U.S. Pat. No. 4,589,965 presents a method for electroblotting, whereby an electrophoretically resolved material in a gelatin sheet is transferred to a membrane. The gelatin sheet is in contact with an immobilizing material, sandwiched between two plate electrodes. U.S. Pat. No. 4,994,166 to Fernwood et al describes a single apparatus for slab gel electrophoresis and blotting, both of which are performed in a single tank cell, which contains separation electrodes along opposing vertical walls and blotting electrodes arranged horizontally above and below the level of gel placement. The cell is operated in separatory and blotting modes, in which separatory and blotting electrodes are separately energized. No means for separation of gel and blotting membrane are provided.

U.S. Pat. No. 4,812,216 to Hurd explain a method and apparatus for supporting and handling blot membranes during the course of blotting, analysis, and storage. U.S. Pat. No. 5,039,493 to Oprandy describes a positive pressure blotting apparatus having a bottom section, a middle section, and a top section. The first volume of space is encompassed between the top section and the middle section. Positive pressure is maintained in the first volume of the apparatus. A hydrophobic filter means for binding biological materials is positioned on, or in, the middle section, and a means is provided to secure the top, middle and bottom sections together to form a pressure blotting apparatus. U.S. Pat. No. 5,149,408 to Perlman shows a capillary blotting sandwich for transferring soluble macromolecules in a liquid medium from a liquid-permeable matrix to a semi-permeable receiving membrane. The blotting sandwich includes: (i) a liquid-permeable matrix layer comprising soluble macromolecules, said matrix having at least one flat surface; (ii) a semi-permeable membrane sheet layer disposed on said flat surface; (iii) an interlocked hydrophilic absorbent fiber-containing material in the form of a non-woven absorbent felt sheet, which facilitates capillary transport of a solution through said membrane.

U.S. Pat. No. 5,013,420 to Schuette presents electrophoresis-blot transfer apparatus, in which a buffer tank is common to both the electrophoresis and electro-blot transfer. Combination of two procedures (separation and transfer) requires a two-step operation with reassembly of an electro-blot sandwich. U.S. Pat. No. 4,889,606 to Dyson et al describes a method and apparatus for use in electrophoresis and blotting, in which electrophoresis is carried out on a gel, supported by a rigid porous plate. The gel is cast onto the porous plate with a transfer membrane between the porous plate and the gel. The method consists of the first stage, using electric field produced by electrodes to draw the samples through the gel; and the second stage, drawing the distributed macromolecules onto the transfer membrane. Since separating gel and transfer membrane are not separated by a barrier, contamination of the blotting membrane occurs while separation. U.S. Pat. No. 4,589,965 to Kreisher describes a method for electroblotting, whereby an electrophoretically resolved material in a gelatin sheet is quickly and efficiently transferred to a membrane with high pattern definition and resolution.

U.S. Pat. No. 5,593,561 to Cognard and Hache shows a multiple electrophoresis method for controlled migration of macromolecules and transfer thereof to the membrane in a vessel, containing a plurality of parallel elongate electrodes. The first electric field, established between electrodes, provides means for macromolecular separation in a gel, and the second electric field, perpendicular to the first, provides means for transferring the macromolecules onto the membranes. In the described method, at first, electrodes and transfer membranes are assembled in the vessel, which is then filled with gel. After the separation of macromolecules in a gel and transfer to membranes, gel is liquefied, dissolved, or decomposed, allowing the removal of membranes. Closely related U.S. Pat. No. 5,102,524 to Dutertre describes a multiple electrophoresis method, where different sets of electrodes are used in a two-step process to first separate macromolecules and then to transfer them to a deposition membrane. No means to separate the deposition membrane from the gel during the first step of electrophoresis are provided. U.S. Pat. Nos. 4,849,078 and 4,911,816, both to Love et al, present apparatus for carrying out horizontal electrophoresis and subsequent vacuum-assisted transportation of macromolecules to a support membrane. Process is performed in two steps: first, electrophoresis is performed; and second, deposit membrane is put in contact with gel, and vacuum transfer is conducted.

U.S. Pat. No. 5,217,592 to Jones describes apparatus, which includes the combination of submarine gel tank for electrophoresis separation with a vacuum applying means, which transfer the separated molecules from the gel into the deposition membrane, to a filter membrane by means of controlled vacuum. No means to separate the deposition membrane from the gel during the first step of electrophoresis are provided. U.S. Pat. No. 5,155,049 to Kauvar teaches a technique for passage of liquid through a membrane putatively containing in its interstices at least one substance, for which detection is desired. Further, it comprises positioning donor and acceptor bibulous matrices onto either surface of the membrane, squeezing the resulting sandwich. This technique permits the application of small volumes of reagents or wash to the membranes and the facile recovery of the waste.

U.S. Pat. No. 5,445,723 to Camacho describes blotting apparatus for transferring electrophoretically separated molecules from the gel into a transfer stack. Apparatus includes a resilient anode surface for transfer of molecules, which is mounted on a mechanical carrier arm, which moves the anode surface over the membrane during transfer—mechanically moved device.

U.S. Pat. No. 5,234,559 to Collier et al explains an apparatus for direct blotting and automated electrophoresis, transfer, and detection of biomolecules. Separation and transfer module consists of a separating gel and transfer membrane, stabilized by a frame, which is moved mechanically in orthogonal direction to the gel. Moving frame with the membrane is in contact with the edge of the gel, towards which separated fragments are driven electrophoretically.

U.S. Pat. No. 5,279,721 to Schmid describes an automated electrophoresis and transfer apparatus for separating macromolecules and blotting them to a transfer membrane, which includes a housing having a perforated intermediate horizontal partition defining an upper reservoir and a lower chamber. A transfer membrane is positioned over the partition; an impermeable sheet is interposed between the membrane and the gel member and withdrawn prior to transfer operation. Cooperation with the impermeable sheet substantially prevents chemical solutions from permeating the transfer membrane prior to transfer operation. In this embodiment, subdivision of separation and transfer processes is provided by means of mechanically moving an impermeable membrane.

U.S. Pat. Nos. 4,631,120 and 4,631,122, depict apparatus and method for a direct blotting process, which provides one or more collecting surfaces mounted on a conveyer belt or tape and advances the belt so that it slides over the end of the gel to collect separated particles and transport them with the belt away from the gel to a location, where further processing may be performed. Both vertical and horizontal embodiments are disclosed. Contact of this nature is damaging to the surface and may remove separated material. Also apparatus does not allow handling and identification of a multiplicity of samples in sequence. U.S. Pat. No. 5,514,256 to Douthart et al describes a direct blotting electrophoresis unit for DNA separation. The DNA sequence is deposited on a membrane attached to a rotating drum. Separation of DNA is performed in a capillary-like mini-gel system. A rotating drum with a deposition membrane is adjacent to the edge of the gel, and transfer of molecules to the gel occurs by means of electrophoretic transfer.

Claimed apparatuses and methods possess substantial disadvantages: after separation is completed, direct blotting in combination with slab gel electrophoresis requires mechanical means for changing the configuration of the system in order to put the blotting element in contact with separating gel. In capillary electrophoresis system, direct blotting appears to be impossible because a very thin layer of interactive matrix is in a very close proximity to the walls.

Use of semipermeable membranes for assisting the capillary separation has been claimed previously, though for different purposes. For example, U.S. Pat. No. 5,985,121 to Wu et al describes apparatus for capillary electrophoresis carrying out on-line sample preparation by means of a semipermeable membranes connected to the capillary separation column for selective introduction of ampholytes into the capillary separation column. Transfer procedures are not described in this invention. U.S. Pat. No. 5,338,427 to Shartle teaches a disposable cartridge for a capillary electrophoresis instrument, in which short capillary tube segments are used for simultaneous multiple lane separations. The cartridge contains all separation components of the instrument, which come in contact with the sample and is capable of automatically loading a quantitative portion of a bulk sample into the capillary tube segments. Electrophoresis occurs without bulk flow through the capillaries, which are scanned in situ by the instrument. U.S. Pat. No. 5,169,511 depicts capillary tube for electrophoresis with a sample cup, consisting of two wells, bottoms of which are covered with semipermeable membrane. Membrane allows the flow of buffer, but not the migration of separated sample. U.S. Pat. No. 5,482,613 describes a method for making a gel plate with a microporous membrane by means of rectangular frame cassette and means of tensioning a membrane deposited on a frame. U.S. Pat. No. 4,512,896 to Gershoni teaches a method of transfer of macromolecules to a mobilizing matrix, which is a charge modified microporous membrane. U.S. Pat. No. 5,897,817 shows a process for making medical device from a cellulose acetate hollow fiber semipermeable membrane. In this process, a molten liquid, comprising cellulose acetate, is extruded to produce a membrane. The solvent and the non-solvent are removed from the membrane to produce a semipermeable membrane, having water permeability. The semipermeable membrane can be incorporated in casing in order to produce a product. U.S. Pat. No. 5,131,994 to Shmidt and Cheh explains a method and apparatus for affecting an electrophoretic separation of charged particles. Fractionation chamber comprising a semipermeable membrane is used, wherein a trans-membrane force holds the particles to be separated against the membrane surface, while a voltage gradient is applied to separate particles. U.S. Pat. No. 4,964,961 to Brautigam and Gorman describes apparatus for electroelution of components, separated by preparative electrophoresis on a gel comprising a means for separation of molecules and elution of a selected fraction through a side of separation vessels using a dialysis membrane.

U.S. Pat. No. 5,840,169 to Andersen presents an apparatus and process for electroelution of a gel, comprising of a device with parallel adjacent chambers. Gel with separated macromolecules is placed on top of the apparatus; and electroelution occurs through a semipermeable membrane, placed on the other open sides of the chambers. Macromolecules in the gel migrate into the elution buffers in the chambers. Apparatus and method do not provide means for blotting.

U.S. Pat. No. 5,284,559 to Lim and Hixton describes device for electrophoresis comprising of a pair of spaced apart plates with a separating gel in between and a semipermeable membrane connected to the end of the plates. Membrane forms a collection channel for receiving molecules, which have traveled through the gel, and allows performance of fraction collection. Means for blotting are not disclosed. U.S. Pat. No. 5,427,664 to Stoev demonstrate a free solution electrophones-membrane-filter trapping assay apparatus, which includes a container and at least one porous membrane. The porous membrane and container define a chamber capable of holding run solution. A specimen containing particles to be classified is juxtaposed with the run solution. Particles, which are smaller in size than the pores of the membrane, pass through the membrane, while particles having a larger size do not. A method of classifying particles includes steps providing a sample of particles and a porous membrane, positioning a run solution between the sample and the membrane, and applying an initial voltage across the sample, run solution and membrane.

U.S. Pat. Nos. 4,992,172 and 5,160,626, both to Pemawansa et al, are examples of various membrane compositions, including the ones, which use microporous composites for direct blotting. U.S. Pat. No. 4,992,172 describes a blotting composition, comprising a substrate applied to an activated microporous membrane comprising a membrane polymer and having (1) an internal surface comprising interstices or pore surfaces and (2) an external surface; wherein substantially all said surfaces of the microporous membrane are coated without significant chemical reaction to substantially all said available surface areas of said microporous membrane and thereby activated by a polyaldehyde-containing mixture in an amount sufficient to effectively activate the microporous membrane; and wherein the mixture is soluble enough to penetrate substantially all said interstices of the microporous membrane without substantial damage to the pore structure. Means of separation and/or modification of membranes in the process of transfer are not claimed. U.S. Pat. No. 5,160,626 describes a method of transferring a biological sample to an immobilizing matrix, comprising applying the sample to an activated microporous membrane having: 1) an internal surface comprising interstices or pore surfaces; and 2) an external surface, which membrane comprises a membrane polymer that is non-covalently activated by having all said surfaces of the membrane physically coated with a polyaldehyde mixture in an amount sufficient to provide effective free aldehyde functionality on said surfaces for covalent bonding between the thus coated membrane and aldehyde reactive material of said sample and to thereby non-covalently activate the microporous membrane for said bonding without substantial damage to the pore structure. Means of combined separation and blotting are not disclosed.

The major disadvantage of the prior art is that the methods and apparatuses described allow performing only one of the two processes at a time and require a mechanical rearrangement of the geometry of the system to combine blotting and separating elements. Two separate units increase cost, labor and time of the procedure, which is a significant disadvantage with conventional devices. Mechanically based devices are complex and expensive; they cannot be used as disposables. In a standard setup for capillary separation molecules of interest, if direct blotting to the walls of the capillary is attempted, the molecules of interest will be attached to the walls along the whole length of the capillary, making distinction impossible. For that reason, the entire wall of the capillary element must be inert and should not allow any interaction between walls and separated molecules. Thus, detection of capillary electrophoresis or chromatography was previously possible only at the exit end of the capillary. The method of the instant invention allows modification of chemical properties of the walls of separating element, so that walls are transformed from impermeable to permeable state after separation by means of chemical or physical modification and thus allow a free passage of separated molecules towards the blotting element through the walls of the capillary. Previously described capillary-based separation techniques do not allow to perform separation and direct blotting, as they require detection or blotting only after separated materials leave the capillary. In formerly described capillary separation devices, these processes cannot be combined together in one capillary element. The capillary electrophoresis system and method of the instant invention have solved these problems of prior art systems.

It is an object of the present invention to provide an apparatus that positions a transfer membrane (blotting membrane) relative to a separating element (sieving or interacting matrix such as gel) by means of permeable membrane, whose properties can be chemically or physically modified, and when the gradient of driving forces is changed from the direction of separation to direction favorable to transfer, the transfer to the membrane is conducted in a time-controlled fashion. It is a further object of the present invention to combine separating element and blotting element in one composite to eliminate the necessity to perform two separate processes—separation and blotting. A feature of the present invention is the means to provide a combined apparatus for separation and blotting in one capillary-based unit with means of direct blotting to the walls of a disposable capillary. It is yet another advantage of the present invention, that it allows to use very long capillary elements, where length to diameter ratio of capillary can be more than a 100, thus providing a high resolution of separation. It is a further advantage of the present invention that the apparatus and method disclosed are amenable to automated process and allow to provide uniform, repeatable and well-controlled conditions for performing separation and blotting even in non-specialized environment (field environment). These and other objects, features and advantages of the invention will become apparent upon having reference to the following description of the preferred embodiments. The present invention meets the above objectives and provides advantages theretofore unavailable in conventional devices.

BRIEF SUMMARY OF THE INVENTION

The invention is directed to a system for separation of macromolecules according to their dimensions and/or charge (capillary or blot electrophoresis or gel chromatography) and method for precise post-separation blotting of said molecules to the accepting element. A disposable separation element (capillary) contains inside a sieving or interaction matrix; an external layer of blotting material, positioned close to the boundary of said sieving or interaction matrix; and/or a membrane with changeable permeability for separated material, which separates blotting layer from the sieving or interaction matrix. After separation of macromolecules in capillary with initially non-permeable walls, physical of chemical modification of the intermediate membrane is performed, which is followed by change in the vector of driving forces for transfer, so that separated molecules are moved through the walls of the capillary and blotted to the outer layer of blotting material. The system of the invention includes a disposable separation element (capillary), which can be stretched or coiled inside reservoir; an electrophoresis buffer reservoir to supply electrophoresis buffer to the entrance and exit of the capillary; reservoirs to supply buffer; and modifying solution to a blotting material positioned as an outer layer at the body of capillary element. Means of modification of separation membrane include, but not limited to, chemical or physical modification to change permeability of the membrane for separated material after accomplishment of the separation in said sieving or interaction matrix. Change in driving force for the separation material may include, but is not limited to electrical charge application, bulk flow of fluid, hydrostatic pressure, or gravity.

Post-blotting processing of the sample components in the said system can include any type of analysis, reaction, modification, collection, or purification. For example, the blotting element may be used to transfer the separated and blotted sample components to analytical devices and/or further processed in antigen-antibody reaction or hybridized with DNA or RNA probes. Also blotted samples may be purified or processed by radioactive analysis or electrochemical analyses.

DETAILED DESCRIPTION OF THE INVENTION

Figure 1:
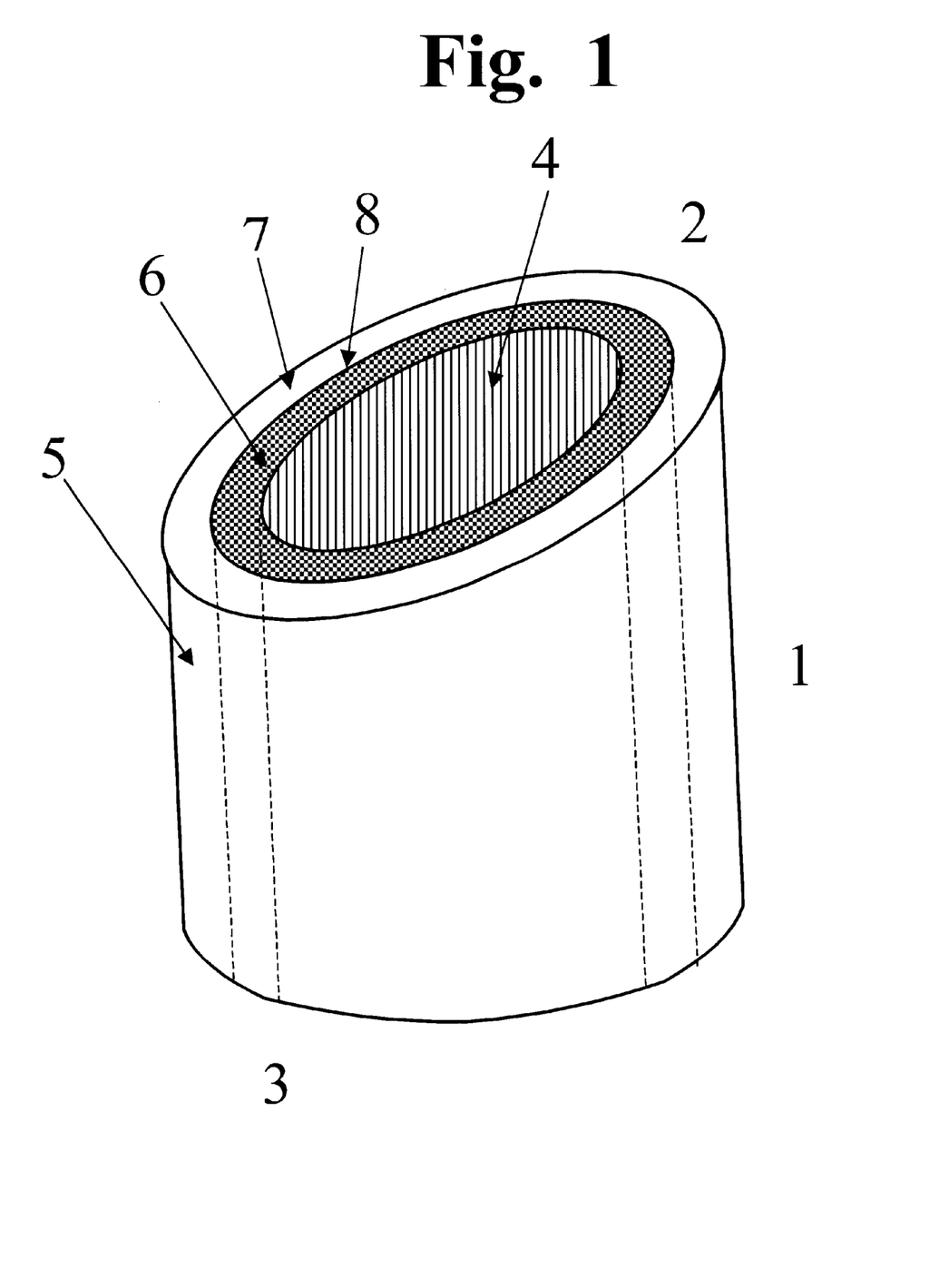
FIG. 1. Arrangement of separating and deposition membranes in a separating element.

In FIG. 1, a diagram of a separating element is shown. The separating system comprises of a capillary tube 1 with an entrance end 2 and an exit end 3. Capillary is filled with separating media or interactive matrix 4. Sample is introduced into the entrance end and enters the capillary tube by a pipette, hydrostatic flow or by electromigration and/or electroosmosis. Walls of the capillary tube 5 are made of the first layer of semipermeable separating membrane with changeable permeability 6, and the layer of deposition membrane 7. The membrane contains electrolyte in order to maintain electrical contact between electrode and deposition membrane. The boundary between layers 6 and 7 may be comprised of an additional layer of porous material 8. A key component of the apparatus of an instant invention is a unique unit with chemically or physically modifiable membrane 6, which allows direct blotting of the separated proteins or sequence ladders onto a nylon or another suitable deposition membrane affixed to external surface of the separating membrane.

The basis of the method of a present invention is membrane 6, with changeable permeability characteristics (Kesting, R. E. *Synthetic polymeric membranes.* John Wiley and Sons, Inc., 1985, p. 224–329). Such membrane separates the interactive matrix 4 in the capillary and deposition membrane 7 and thus forms a structure of the capillary wall. This membrane can be made of a variety of materials and utilize a variety of methods to modify its permeability. One of the examples of separation membranes is a phase inversion process of membrane formation, in which polymer solution (in which the solvent system is in continuous phase) inverts into swollen three-dimensional macromolecular network or gel (polymer in the gel is a continuous phase). Gel constitutes a phase-inversion membrane. The latent solvent is removed (process named leaching) from the membrane gel after the gel attains sufficient strength. Typical leaching agents include isopropanol, ethanol, heptane, methyl alkyl ketone, and others. The most appropriate leaching processes for the described invention are those, in which preformers are low-molecular-weight surfactants (preferably ionic), which form high molecular weight, evenly dispersed micelles in the fluid state and maintain this structure in the solid polymer matrix. After leaching the solid matrix, the volumes previously occupied by surfactant micelles become pores. Polymer-assisted phase inversion process uses a solution consisting of one solvent and two physically compatible polymers. After solvent evaporation, film is immersed in liquid such as water, which serves as a solvent for polymer, but not the other. The insoluble network remains after leaching, forming microporous polymer-assisted phase-inversion membrane. Polymer, which is leached, serves as a non-solvent pore former ("assistant").

Another example is liquid and dynamically formed membranes. Liquid membranes are thin semipermeable barriers, which are in liquid state. Immobilized liquid membranes are confined within a microporous solid. The most widely used and simplest process of preparing porous membranes is the Gelgard® process, in which the semicristalline films or fibers are extruded from the melt. Porosity induced by stretching solid-state polymer, like polypropylene. Gelgard® is available in both film and hollow fiber form with pore sizes up to 0.04 $\mu$m. Gelgard® hollow fibers are available with 100–1500 $\mu$m ID and 25 $\mu$m wall thickness and are used for example, in blood oxygenators. Gelgard® is compatible with ethyl alcohol, ethylene glycol, and isopropyl alcohol. Another example is Gore-Tex®, microporous poly (tetrafluoroethylene), which is a widely used porous membrane, also manufactured by stretching process. Gore-Tex® is one of the most chemically inert and hydrophobic synthetic polymeric membranes.

Dynamically formed membranes initially exist in the liquid state and are formed into semipermeable barrier layer from suspensions of finely divided particles, when the later are allowed to impinge upon a porous layer. Support liquid membranes are formed by placing liquid membrane on a dense membrane or by internal containment of the liquid membrane within a microporous support. Liquid surfactant membranes are formed by concentration on the interface between a liquid solution and a dense membrane. The bilayer of dense membrane and surfactant membrane provides a composite structure, whose components act in series to provide permeability characteristics of the particular membrane. Liquid surfactant membranes can form spontaneously on every impermeable interface, which is in contact with surfactant solution. Surface films of soluble surfactants influence material transport across phase interfaces in the same manner as insoluble films. Internally supported membranes can be used for facilitating selective transport across porous membranes. Variation in permeability and permselectivity of various liquid-surfactant membranes is due to two main factors: hydrophilic/hydrophobic balance and packing arrangement within and between individual micelles.

Separating membrane 6 with changeable permeability characteristics can be made by process of leaching of the preformed membrane; by changing permeability of liquid-deposited, liquid surfactant membrane by changing chemical composition, pH or the temperature of the surrounding buffering solution 11. Leaching of the solid matrix of membrane makes pores in volumes previously occupied by surfactant micelles. For example, such porous membrane can be made from mixture of viscose solution and 200% sodium dodecyl benzene sulfonate (R. E. Kesting, *Synthetic Polymeric Membranes.* John Wiley and Sons, Inc. 1985, p. 224–329). The preferred leaching agents are water, lower alcohols or toluene. After solidification of the polymer, it can be swollen in liquid, which has the effect of breaking down the micelles of surfactant to individual molecules and their rapid extraction. Leaching of the surfactant micelles can be applied to a variety of solutions, including cellulose and methoxymethylated nylon, polyacrilic, poly (vinyl acetate), and polyethylene-paraffin. For example, lauryl pyridinium chloride in toluene can be utilized as the surfactant micelle to form a microporous polyethylene membrane.

Liquid-surfactant membranes can be precoated on a dense supporting membrane, for example by coating the membrane substrate with 0.1% solution of poly (vinyl methyl ether) in $CCl_4$. Internal support to liquid membranes can be provided by several ways, for example by addition of a gelling agent such as Cabosil® or Cellosize®, confinement of liquid membrane with a microporous support (immobilized membrane), deposition of a film such as poly (vinyl methyl ether), which is potentially soluble in water, and controlling swelling by introduction of covalent cross-links.

For dynamically formed membranes support like any suitable filter or hollow fiber can be used. Phospholipid layer is an example of temperature-sensitive permeability membrane (Sada, S., Katoh, S., and Terashima, M. Transfer of solutes through composite membranes containing phospholipids. In: *Membranes and Membrane Processes*. E. Drioli. M. Nagasaki (Ed.), Plenum Press, N.Y. (1986), pp. 455–459), where permeability characteristics change by an order of magnitude around the melting temperature of phospholipids.

Other polymeric substances, which can be used for these purposes, are, but not limited to, starch sulfate, Sephadex (dextran) polyacrylic acid, sulfonated polysterene, poly (vinyl pyrrolidone), hydroxyethylcellulose, poly (ethyleneoxide) and its block copolymers, and poly (propylene oxide). Permeability and permselectivity of positively charged membranes is a function of pH and temperature. Membranes can be made wet by contacting the membrane with a water miscible organic solvent such as ethanol, methanol, acetone, or the like. Representative membranes may include polyolefins such as polyethylene, polypropylene, polymethylpentene, or the like; polystyrene or substituted polystyrenes; fluorinated polymers including poly (tetrafluoroethylene), polyvinyldiene fluoride, or the like; polysulfones, such as polysulfone, polyethersulfone, or the like; polyesters including polyethylene terephthalate, polybutylene terephthalate, or the like; polyacrylates or any polycarbonates; polyamide nitrocellulose, vinyl polymers such as polyvinyl chloride, copolymers of butadiene and styrene, fluorinated ethylene-propylene copolymer, ethylene-chlorotri-fluoroethylene copolymer, or the like. Deposition membrane element 7 comprises an electrically conductive layer electrically connected to a source of electrical energy through the buffering electrolyte solution made of a material suitable for deposition of protein or DNA molecules, like for example, nitrocellulose paper, nylon, and others.

Figure 2:
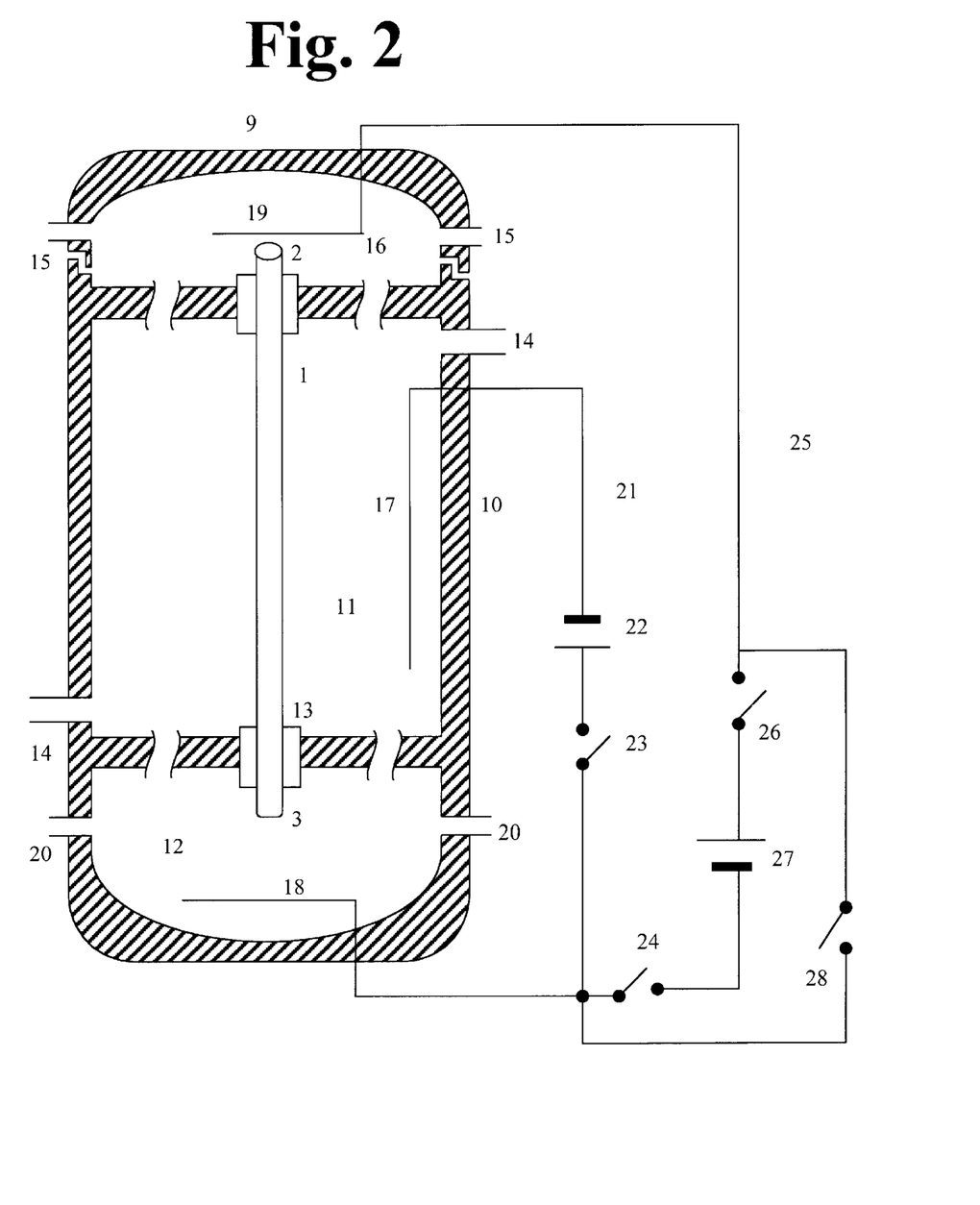
FIG. 2. Unit for the capillary electrophoresis—direct electro-blotting.

The diagrammatic scheme of a separating apparatus, based on the above-described separating element 1, is shown in FIG. 2. Referring to FIG. 2, the capillary 1 is submerged into reservoir and support structure 10, filled with buffering solution 11. Reservoir 10 can be in the form of rectangular parallelepiped or in the form of cylinder. Reservoir 10 may contain multiple separating elements 1. A separation-blotting system of the invention includes, in general, an array of capillaries 1. Capillary 1 is in contact at the loading end 2 with a capillary electrophoresis buffer reservoir 16 and at the exit end 3 with a capillary electrophoresis buffer reservoir 12. Buffer, contained within reservoirs 10, 12, 16, can be any buffer commonly used in capillary electrophoretic separation: a Tris buffer or a phosphate buffer. Capillary electrophoresis reservoir 16 and collection buffer reservoir 12 are in electrical contact through electrodes 19 and 18, respectively, and are connected to a high voltage power supply 27 to provide electrical current. An additional electrode structure of this invention comprises an electrically conductive wire 21 connected to power supply 22. The electrically conductive wire 25 is connected to the electrical battery or electrical power supply 27 through switches 24 and 26, which are turned on during the separation phase and are turned off during the blotting phase.

Support structure 10 is a generally circular reservoir or rectangular block of electrically insulating material. Reservoir 10 has at least two separate electrolyte and buffer fillings, which are represented in the form of ducts 14, each including opening and closing means (for example mechanically operated stop-cocks or solenoid valves). One of the ducts is provided at the bottom of reservoir and the other one at the top. According to the invention, these ducts 14 are used for multiple purposes: to fill the reservoir with electrolyte or buffer, to provide circulation of the buffer between reservoir 10 and heat exchange unit to provide means for cooling the set of capillaries during separation phase. Reservoirs 12 and 16 have openings 20 and 15 respectively, which serve the same purposes. The reservoir 10 includes electrodes 17, which are constituted by electrically conductive metal wires and are connected by the electrically conductive wire 21 at their ends to power supply 22 for applying electrical potentials during the blotting phase. The electrode structure 17 can be flat or cylindrical structure. Capillary tube 1 can be supported by an additional supporting structure 13 for mechanical stability. Capillary tube 1 may have support structures made of any clear, low reflection, low absorbance material such as plastic, glass, or silica. Capillary tube 1 is usually from about 1 to about 10 cm in length, although longer length may be used.

Devices may be fabricated from a wide variety of materials, including glass, fused silica, acrylics, thermoplastics and the like. The components may be fabricated from the same or different materials, depending on the particular use of the device. For example, materials like polymethylmethacrylate, polycarbonate, polyethylene, polystyrene or styrene copolymers, and the like. The devices may be fabricated using any convenient means, including casting techniques, by etching or laser micromachining.

The apparatus of the invention is then used as follows:

1. Application of sample and separation of sample. Array of capillaries 1 are placed in chamber 10 and fixed. Chamber 10 and 12 are filled with electrolyte buffer. The lid 9 is opened and samples are deposited at the entrance end 2 of the capillary 1. Then lid 9 is closed and upper chamber 16 is filled with electrolyte buffer through openings 15. Different electrical potentials are applied to electrodes 19 and 18 to create an electrical field between the entrance end 2 and exit end 3 of the capillary, causing the macromolecules to move through the gel, until separation is completed. During this separation phase switches 23 and 28 are opened and switches 24 and 26 are closed. Other means of separating macromolecules (for example gradient of hydrostatic pressure) may be applied instead of electrical field at this stage.

2. Modification of the capillary wall-separating membrane. After separation is complete, electrical switches 24 and 26 are opened. Modification of the separating membrane is achieved by means of changing chemical composition of the buffer solution in chamber 10, or changing its temperature or pH. After a certain amount of time, required for the modification of the membrane to be completed, buffer or other solution is washed from chamber 10, and it is filled with electrolyte buffer.

3. Blotting by change in the gradient of driving force. Electrical switches 24 and 26 remain opened, electrical switches 23 and 28 are closed. Electrode 17 in chamber 10 thus becomes a cathode and electrodes 19 in chamber 16 and electrode 18 in chamber 12 with the capillary structure 1, form an anode. Established electrical driving force moves separated macromolecules in capillary structure 1 in horizontal direction through the membrane 6. Macromolecules are then deposited on the blotting membrane 7.

Other means of transferring macromolecules, for example gradient of hydrostatic pressures, which will cause the flow of fluid through the capillary from reservoirs 12 and 16 into reservoir 10, can be used instead of electrical force. Negative pressure in reservoir 10 can be also applied through ducts 14.

Figure 3:
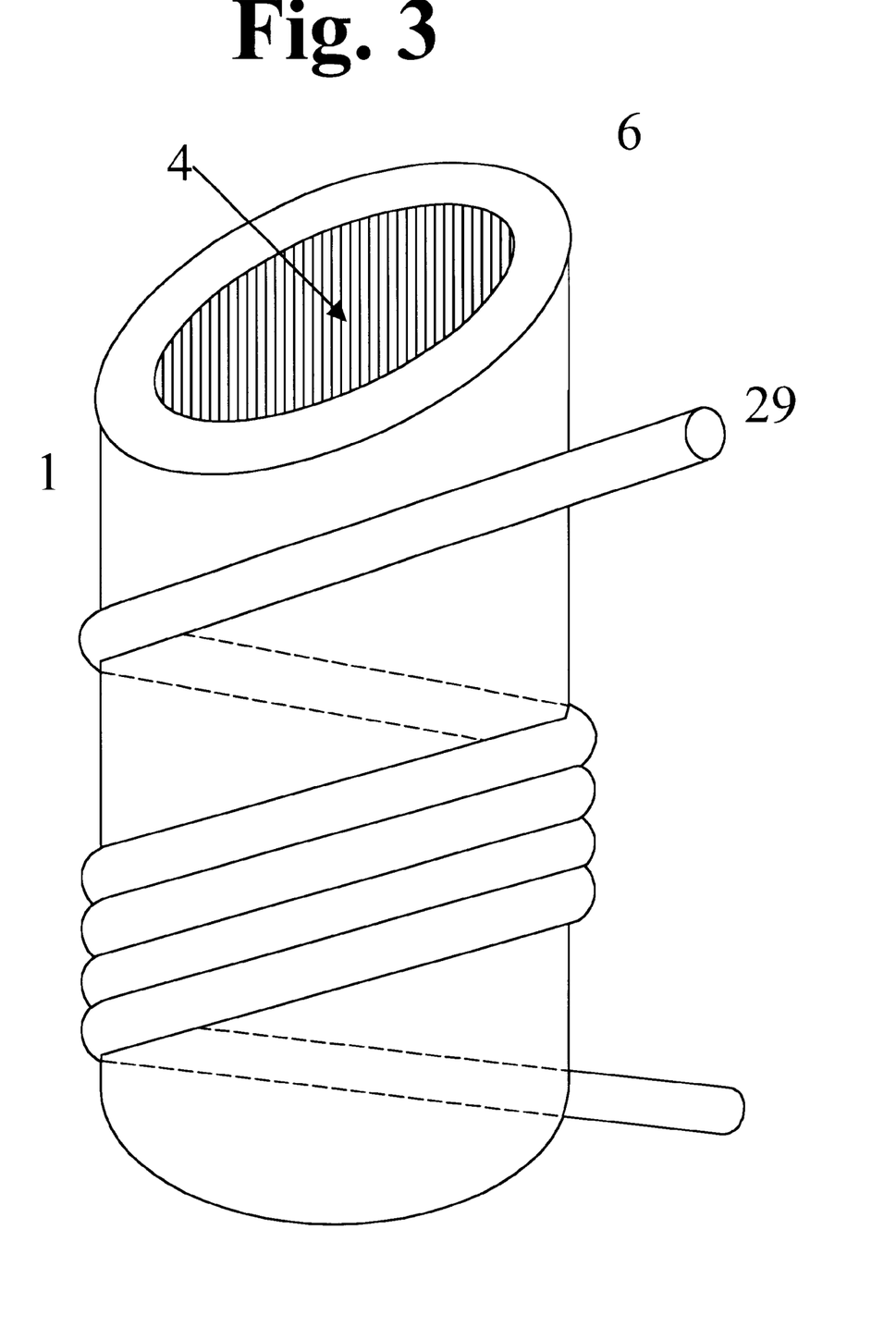
FIG. 3. Positioning of the blotting element by rewinding the deposition material around the separating element.

4. Processing and detection. After a certain period of time macromolecules become fixed on the blotting membrane 7, after which the current is disconnected. The respective fixing solutions or means of detecting macromolecules on the blotting membrane may be applied into chamber 10. The outer wall of the capillary element becomes a carrier of a blotted material, which can be further processed for specific detection. In other embodiments the deposition membrane can be removed without disturbing the separation membrane. The deposition membrane can then be moved intact to suitable downstream detection and processing units. FIG. 3 shows an example of such method, where a thread 29, made of a composition amenable for blotting, is winded around the capillary 1. After blotting is completed, element 29 can be easily unwind and stored for purposes of detection of separated molecules.

The capillary unit of the instant invention has both the data compaction and energy dissipation characteristics of gel-filled capillaries and the ease of preparation, reliability, and easy recasting characteristics of slab gels. The separation capillary can also be formed as a channel or a groove or micromachined on a planar surface or molded in a block of a suitable polymer (Plexiglas or polycarbonate), or on a microchip (Regnier, F. E., He, B., Lin, S., and Busse, J. Chromatography and electrophoresis on chips: critical elements of future integrated, microfluidic analytical systems for life science. *Trends Biotech,* 1999, Vol. 17, no. 3:101–116; U.S. Pat. No. 6,007,690 to Nelson et al). Electrophoretic separation can be carried out with or without the use of a sieving or interaction matrix and in combination with any other appropriate technique, such as isoelectric focusing. In addition, separation can take place in an open tube as capillary zone electrophoresis, with or without the use of electroosmotic flow. After deposition of the sample on the deposition membrane, the sample can be reacted with conventional reagents used in available assay or detection techniques (radio-labeled or fluorescent labeled antigens or antibodies, staining reagents or dyes).

The described apparatus and method allows combination of advantages of capillary electrophoresis and direct blotting in one single element. Multiple arrays of such elements allow performing numerous sample analyses in short periods of time automatically, saving labor and time. Optimization of geometrical variables allows using very small volumes of expensive reagents, like antibodies.

EXAMPLE

To demonstrate the potential applicability of the described process and apparatus to the commonly used procedures, Southern and Western blot procedures were performed with DNA samples and tissue protein samples. In Southern blotting procedure samples of prokaryotic DNA from cultures transfected with plasmids carrying sequence for I–II loop of $\alpha_1$ subunit of L-type calcium channel were separated using the described procedure, blotted and probed for the presence of sequence of interest. In Western blot procedure presence of β subunit of L-type calcium channel was determined in protein extracts from heart tissue. To perform capillary electrophoresis, Gelgard® hollow fibers were used. For Southern analyses 6 cm long fibers were filled with 1% agarose solution at 80° C.; and for Western analyses—with 10% polyacrilamide solution at 50° C., both of which become gels upon cooling to room temperature. Walls of capillary fibers were bathed in a mixture of organic triglycerides at 50° C., removed, cooled to room temperature, washed in buffer, and wrapped in nitrocellulose paper (Hybond, Amersham Pharmacia Biotech) in a manner, shown in FIG. 3. The resulting capillary element was placed in the electrophoresis bath, schematically depicted in FIG. 2. Element contacts with walls, which separate the reservoirs, were sealed with glue. Samples of procariotic DNA were digested with EcoRI and introduced into the entrance of the capillary with syringe for chromatographic sample injection. Positive controls were samples of DNA from transfected cultures of *E. coli* expressing I–II loop of L-VDCC; negative controls were wild type cultures. Separation was performed at 150V with potential difference of 10 min; temperature of bath was kept below 10° C. After electrophoresis separation element was washed several times in elution buffer with methanol concentration of 40% at 60° C. by changing solution in intermediate reservoir. Transfer to nitrocellulose membrane was performed in 10 min by changing the electrophoretic gradient, as described in the summary of the invention. After transfer the nitrocellulose paper was detached from the separating element, the DNA was probed with a 1350 bp EcoRI digested complementary fragment from the full-length $\alpha_{1C}$ cDNA (bases 2098–3448). As a control, standard procedures of Southern blotting, utilizing slab blot electrophoresis and electrotransfer, were used. Both methods showed presence of DNA fragment of interest (I–II loop of L-VDCC) in positive controls and its absence in negative controls. Capillary transfer was accomplished in a small fraction (10%) of time required for standard procedure without mechanical transfer of elements.

Western blot analysis of the β-subunit was performed in the same manner. Protein extracts from mice hearts were prepared by standard techniques. Membrane and cytosolic fractions (0.5 µg) were introduced into separating capillary elements, separated and transferred as described above to nitrocellulose membranes (Hybond-ECL, Amersham Pharmacia Biotech). Nitrocellulose membranes were then detached from separating element, blocked with 5% nonfat milk for one hour at room temperature (22–25° C.). Blots were incubated with $β_1$-subunit of L-type calcium channel primary antibody (Swant) for 1 h at 22° C. Horseradish peroxidase-conjugated secondary antibody was added for 1 hour at room temperature, and the signals were visualized by the enhanced chemiluminescence procedure (Amersham Pharmacia Biotech). Standard stained molecular weight markers (Amersham) were loaded to determine the molecular weight of the fraction. Standard electrophoresis and electroblotting procedure was performed with same samples as a control. Both methods demonstrated similar results of location of fraction of interest ($β_1$-subunit) relatively to the known molecular weight markers.

This example demonstrated that the described apparatus and method allows to shorten time, cost and labor of the procedure, not to mention a possibility of usage of multiple separating elements for simultaneous analyses of a very large number of samples.

Although the invention has been shown and described with respect to illustrative embodiments thereof, it should be appreciated that the foregoing and various other changes, omissions and additions in the form and detail thereof may be made without departing from the spirit and scope of the invention as delineated in the following claims.

What is claimed is:

1. An apparatus for combined separation and blotting of biomolecules, the apparatus comprising a support structure comprising a disposable separating element having an entrance end, an exit end and a body, external electrodes, side electrodes, and three separate reservoirs: one reservoir in which the entrance end of the separating element is located, one reservoir in which the exit end of the separating element is located, and one reservoir in which the body of the separating element is located, each reservoir having means for leak-proof closure, openings for filling with electrolyte solution, means for circulating fluid, and means for applying pressure within the reservoirs, each reservoir also being filled with buffer solution, which surrounds the separating element;

the disposable separating element comprising at least one capillary tube vertically or horizontally supported by said support structure in a stretched or coiled configuration, said capillary tube having vertically or longitudinally opposed ends and filled with sieving or interaction matrix, a first layer of porous material, which acts as a separating membrane, and a second layer of porous material external to the first layer, which acts as a deposition membrane, the support structure also comprising means for modulating the permeability properties of the first layer of porous material by changing chemical composition, temperature, or pH of the surrounding solution;

the external electrodes being attached on said support structure adjacent to the capillary tube ends and adapted for electrical contacts with the capillary ends when the capillary tube is filled with a conductive solution so electrophoresis of a molecular mixture can be performed in the capillary tube; and the side electrodes being positioned adjacent to the body of the capillary tube so separated material from inside the capillary can be transferred by electrophoresis to said second layer of porous material through the first layer.

2. The apparatus of claim 1 in which the second layer of porous material is blotting material that can be removed from the external surface of the capillary tube.

3. The apparatus of claim 2 in which the blotting material is a layer of thread made of blotting material that has been wound around said capillary.

4. A method for precise separation and post-separation blotting of molecules to a deposition membrane, the method comprising providing a separation system comprising a capillary tube and a deposition membrane comprising blotting material;

separating molecules in the separation system by electrophoresis or gel electrophoresis;

chemically or physically modifying the capillary tube wall to change its permeability to allow free transport of the separated molecules through the capillary tube wall; and applying an electrical or hydrostatic driving force to cause the separated molecules to move through he capillary tube wall and contact the blotting material of the deposition membrane.

* * * * *